(12) United States Patent
Wegrzyn, III (10) Patent No.: US 9,351,767 B2
(45) Date of Patent: May 31, 2016

(54) SUPPLEMENTARY SPINAL FIXATION/STABILIZATION APPARATUS WITH DYNAMIC INTER-VERTEBRAL CONNECTION

(75) Inventor: Thomas J. Wegrzyn, III, Cambridge, MA (US)

(73) Assignee: Life Spine, Inc., Huntley, IL (US)

( * ) Notice: Subject to any disclaimer, the term of this patent is extended or adjusted under 35 U.S.C. 154(b) by 672 days.

(21) Appl. No.: 12/730,940

(22) Filed: Mar. 24, 2010

(65) Prior Publication Data

US 2010/0249843 A1  Sep. 30, 2010

Related U.S. Application Data (60) Provisional application No. 61/162,874, filed on Mar. 24, 2009.

(51) Int. Cl.
*A61B 17/70* (2006.01)

(52) U.S. Cl.
CPC ........... *A61B 17/705* (2013.01); *A61B 17/7011* (2013.01)

(58) Field of Classification Search
CPC ......................... A61B 17/70–17/7046; A61B 17/7074–17/7092
USPC .......... 606/246, 250–263, 278–279, 264–277
See application file for complete search history.

(56) References Cited

U.S. PATENT DOCUMENTS

| | | | | |
|---|---|---|---|---|
| 5,630,816 A | * | 5/1997 | Kambin | 606/252 |
| 5,688,275 A | * | 11/1997 | Koros et al. | 606/264 |
| 5,702,452 A | * | 12/1997 | Argenson et al. | 606/253 |
| 5,716,355 A | * | 2/1998 | Jackson et al. | 606/252 |
| 6,117,135 A | * | 9/2000 | Schlapfer | 606/250 |
| 6,136,000 A | * | 10/2000 | Louis et al. | 606/250 |
| 6,136,002 A | * | 10/2000 | Shih et al. | 606/250 |
| 6,413,258 B1 | * | 7/2002 | Bernhardt, Jr. | 606/252 |
| 6,881,215 B2 | * | 4/2005 | Assaker et al. | 606/250 |
| 7,922,746 B2 | * | 4/2011 | Miller | 606/250 |
| 8,021,399 B2 | * | 9/2011 | Ritland | 606/277 |
| 2002/0143327 A1 | * | 10/2002 | Shluzas | 606/61 |
| 2003/0060823 A1 | * | 3/2003 | Bryan | 606/61 |
| 2004/0153070 A1 | | 8/2004 | Braker et al. | |
| 2004/0254577 A1 | * | 12/2004 | Delecrin et al. | 606/61 |
| 2006/0079892 A1 | * | 4/2006 | Roychowdhury et al. | 606/61 |
| 2007/0043365 A1 | * | 2/2007 | Ritland | 606/61 |
| 2007/0233090 A1 | | 10/2007 | Naifeh et al. | |

(Continued)

OTHER PUBLICATIONS

Bent. (n.d.). Dictionary.com Unabridged. Retrieved Oct. 7, 2015, from Dictionary.com website: http://dictionary.reference.com/browse/bent.*

*Primary Examiner* — Jan Christopher Merene
*Assistant Examiner* — Steven Cotroneo
(74) *Attorney, Agent, or Firm* — Foley & Lardner LLP (57) ABSTRACT

A spinal implant provides supplemental and dynamic fixation and/or stabilization of the spine via connection to one or more existing or new spinal fixation and/or stabilization spinal constructs. The supplementary spinal fixation/stabilization implant has a first attachment device configured to couple to an existing or new spinal fixation/stabilization construct and a second attachment device configured to couple to the existing or new spinal fixation/stabilization construct at a second location. The first and second attachment devices are joined to each other via a resilient connector that allows dynamic movement between the first and second attachment devices.

18 Claims, 6 Drawing Sheets

(56) References Cited

U.S. PATENT DOCUMENTS

| | | | |
|---|---|---|---|
| 2007/0233091 A1* | 10/2007 | Naifeh | A61B 17/7023 606/279 |
| 2007/0270816 A1* | 11/2007 | Rezach | 606/61 |
| 2007/0270837 A1* | 11/2007 | Eckhardt et al. | 606/61 |
| 2008/0262553 A1* | 10/2008 | Hawkins et al. | 606/278 |
| 2008/0306540 A1 | 12/2008 | Mitchell et al. | |
| 2008/0306544 A1 | 12/2008 | Winslow et al. | |
| 2008/0306546 A1 | 12/2008 | Zucherman et al. | |
| 2009/0093843 A1* | 4/2009 | Lemoine et al. | 606/246 |

* cited by examiner

Fig. 6

SUPPLEMENTARY SPINAL FIXATION/STABILIZATION APPARATUS WITH DYNAMIC INTER-VERTEBRAL CONNECTION

RELATED APPLICATIONS

This U.S. non-provisional patent application claims the benefit of and/or priority to U.S. Provisional Patent Application Ser. No. 61/162,874 filed Mar. 24, 2009, entitled "Supplementary Spinal Fixation/Stabilization Apparatus With Dynamic Inter-Vertebral Connection" the entire contents of which is specifically incorporated herein by this reference.

BACKGROUND OF THE INVENTION

1. Field of the Invention

The present invention relates generally to spinal fixation devices for the internal fixation or stabilization of the spine such as spinal implants for holding vertebral bones fixed relative to one another and, more particularly, to spinal implants that are connectable as additive to existing and/or other primary spinal implants.

2. Background Information

Spinal implants have been used for many years to increase spine stability following single and multi-level spinal surgery. Implants such as spine plates, spine rods and spine rod holders, implant assemblies, cross-members and/or the like are implanted during surgery for reasons such as disease, trauma, defect, accident or the like, in order to stabilize and/or fix one or more spinal vertebrae. Stabilization and/or fixation leads to a proper healing and/or a desired outcome. Spinal surgery is thus performed to install the implant(s).

Over time, however, natural wear and tear can diminish or impair the effectiveness of fixation and/or stabilization provided by the existing spinal implant(s). In these cases, it may be necessary to provide re-fixation/stabilization or additional fixation/stabilization that supplements the original fixation/stabilization. Additionally, continued disease, further trauma, accident or the like may also diminish or impair the effectiveness of fixation and/or stabilization provided by the existing spinal implant(s). Again, it may be necessary to provide re-fixation/stabilization or additional fixation/stabilization that supplements the original fixation/stabilization. Sometimes, however, existing spinal implants just require additional, supplemental or auxiliary support or fixation in order to provide the necessary stabilization. Also, it may sometimes be necessary to stabilize one or more additional vertebrae after the initial vertebrae stabilization. In this case, the surgeon must contend with the previously installed spinal hardware.

While current spinal fixation devices may be used as auxiliary or supplemental spinal implants, they are static in nature and thus do not allow or provide for dynamic action.

In view of the above, it would thus be desirable to have a dynamic supplemental spinal fixation/stabilization device.

SUMMARY OF THE INVENTION

The present invention is a spinal fixation/stabilization device that provides supplementary fixation and/or stabilization of the spine via connection to existing spinal fixation and/or stabilization spinal constructs. The supplementary spinal fixation/stabilization device is connectable to existing spinal fixation/stabilization assemblies, constructs or devices for providing supplemental spinal fixation and/or stabilization. The supplementary spinal fixation/stabilization device includes a first connector configured for attachment to the existing spinal fixation/stabilization construct at a first location and a second connector configured for attachment to the existing spinal fixation/stabilization construct at a second location. The first and second connectors are joined to each other via a resilient connector that allows dynamic movement between the first and second connectors.

In one form, the present invention is a supplementary spinal fixation/stabilization apparatus that provides dynamic inter-vertebral connection. The supplementary spinal fixation/stabilization apparatus includes a first connector that is adapted to connect, couple or attach to an existing spinal fixation/stabilization assembly, construct or bone screw assembly that has been affixed to one or more vertebrae, a second connector that is adapted to connect, couple or attach to an existing spinal fixation/stabilization assembly, construct or bone screw assembly that has been affixed to one or more adjacent vertebrae or a new spinal fixation/stabilization assembly, construct or bone screw assembly of one or more adjacent vertebrae, and a resilient and/or elastomeric connector joining the first and second connectors.

The first and second connectors provide fixation to adjacent vertebrae while the resilient/elastomeric connector provides for dynamic (i.e. bending or flexing) between the two connectors.

In one form, the first and second connectors are identical. The first and second identical connectors are configured for attachment to existing spine rods, spine plates and/or other spinal implants or constructs of adjacent vertebrae. In another form, the first connector is configured for attachment to an existing spine rod, spine plate and/or other spinal implant or construct of one vertebra and the second connector is configured for attachment to a spine rod holder/holder assembly of a new or existing spine rod bone screw assembly of an adjacent vertebra.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Like reference numerals indicate the same or similar parts throughout the several figures.

A description of the features, functions and/or configuration of the spine plates depicted in the various figures will now be presented. It should be appreciated that not all of the features of the spine plates of the figures are necessarily described. Some of these non discussed features as well as discussed features are inherent from the figures. Other non discussed features may be inherent in component geometry and/or configuration.

DETAILED DESCRIPTION OF THE PREFERRED EMBODIMENTS

Figure 1:
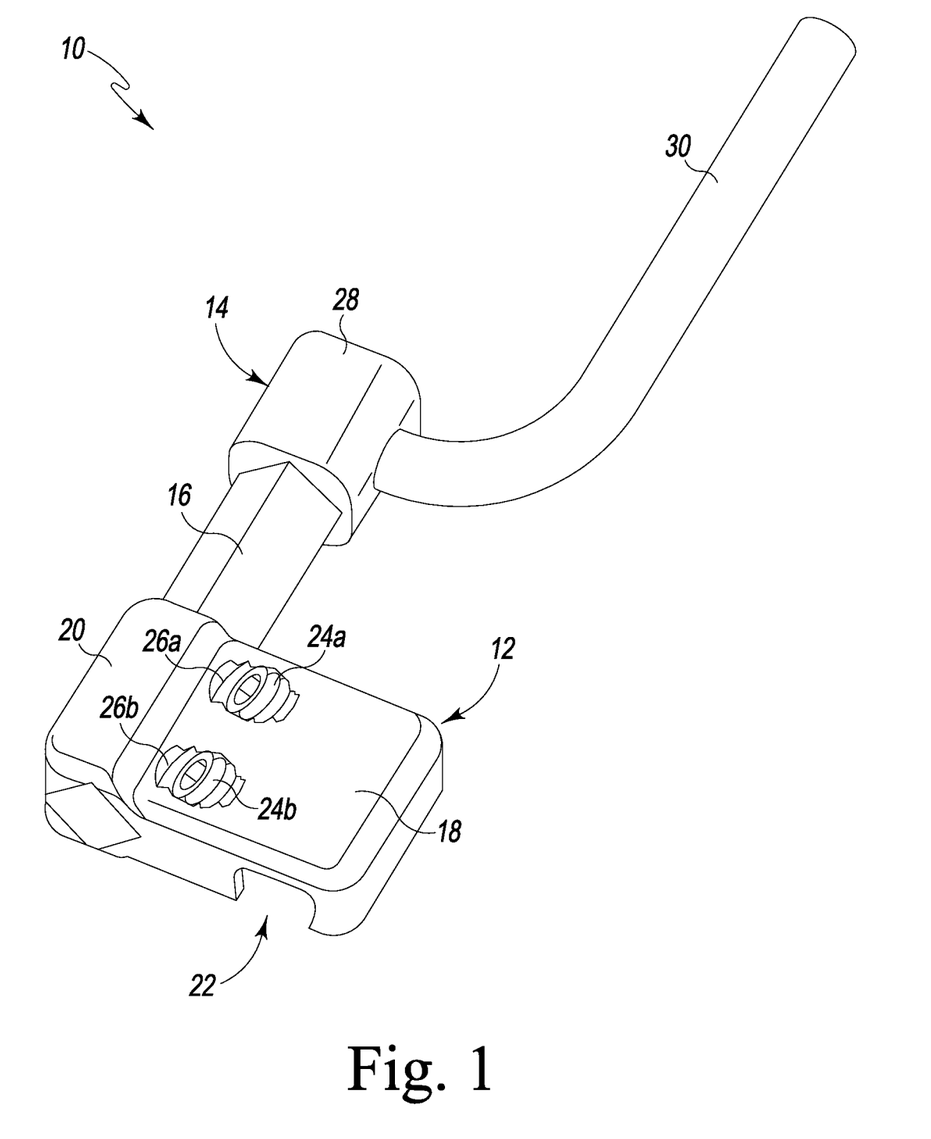
FIG. 1 is an isometric view of an exemplary embodiment of a supplementary spinal fixation/stabilization device providing dynamic intervertebral connection fashioned in accordance with the present principles.

Referring to FIG. 1, there is depicted an exemplary embodiment of a spine or spinal implant embodied as a supplemental or supplementary spinal fixation/stabilization apparatus or device that provides dynamic intervertebral connection (dynamic supplemental or supplementary spinal fixation/stabilization apparatus) generally designated 10 fashioned in accordance with the principles of the present invention. The dynamic supplemental spinal fixation/stabilization apparatus 10 is formed of a suitable biocompatible material.

The dynamic supplemental spinal fixation/stabilization apparatus 10 is characterized by an attachment device or connector 12 that is configured, adapted and/or operative to connect, attach or couple to a previous fusion (e.g. a spine rod, not shown, of a spinal rod fixation device, not shown), a resilient and/or elastomeric connector 16 that is configured, adapted and/or operative to flex and/or bend, and a secondary attachment device or connector 14 that is configured, adapted and/or operative to connect, attach or couple to an adjacent vertebral level in order to prevent it from degenerating further.

The attachment device 12 is made from a biocompatible material such as titanium, stainless steel, PEEK (polyetheretherketone) or the like. The attachment device 12 is formed as a generally rectangular body 18 (other shapes being contemplated) with a generally annular channel or groove 22 extending from one end of the body 18 to the other end of the body 18. The channel 22 is configured to be received on or onto a spinal rod. The attachment device 12 also includes a first set screw 24a that is situated in a first bore 26a. The first bore 26a extends from a top or upper side or surface of the body 18 to a lower or under side or surface of the body 18 that intersects in, terminates in, or opens into the channel 22. The first bore 26a angles into the channel 22 from the upper side of the body 18. The first set screw 24a extends through the first bore 26a and provides contact with the spinal rod that is seated in the channel 22 (see FIG. 2 where end 25b of second set screw 24b can be seen extending into the channel 22). The first set screw 24a thus fixes (or aids in fixing) the attachment device 12 to the spinal rod.

The attachment device further includes a second set screw 24b that is situated in a second bore 26b. The second bore 26b extends from the top or upper side or surface of the body 18 to the lower or under side or surface of the body 18 that intersects in, terminates in, or opens into the channel 22. The second bore 26b angles into the channel 22 from the upper side of the body 18. The second set screw 24b extends through the second bore 26b and provides contact with the spinal rod that is seated in the channel 22 (again, see FIG. 2 where end 25b of second set screw 24b can be seen extending into the channel 22). The second set screw 24b thus fixes (or aids in fixing) the attachment device 12 to the spinal rod.

The attachment device 12 moreover includes a reinforced or raised rear portion 20 through which one end of the elastomeric connector 16 extends and/or is received (an end of which can be seen in FIG. 1). The elastomeric connector 16 is non-rotatably held by the portion 20 and is shown as a generally square (rectangular) rod. Other shapes are contemplated whose shapes aid in preventing twisting or rotation between the attachment device 12 and the secondary attachment device 14. The other end of the connector 16 is received by/in the secondary attachment device 14. Particularly, the other end of the connector 16 is non-rotatably received by or in a generally tubular body 28 of the secondary attachment device 14. The secondary attachment device 14 further includes a rod 30 that is configured for attachment to an adjacent further rod attachment device (i.e. one or more spine rod holders of one or more spine rod bone screw assemblies—not shown) in an adjacent vertebra. The rod 30 is retained in the adjacent further rod attachment device of the adjacent vertebra (not shown).

The attachment device 12 is fixed to an existing spinal fixation/stabilization assembly while the secondary attachment device 14 is fixed to an adjacent level spinal fixation device. The elastomeric connector 16 thus provides flexing or bending relative to the attachments devices 12, 14 and thus between the vertebrae to which they are fixed.

Figure 2:
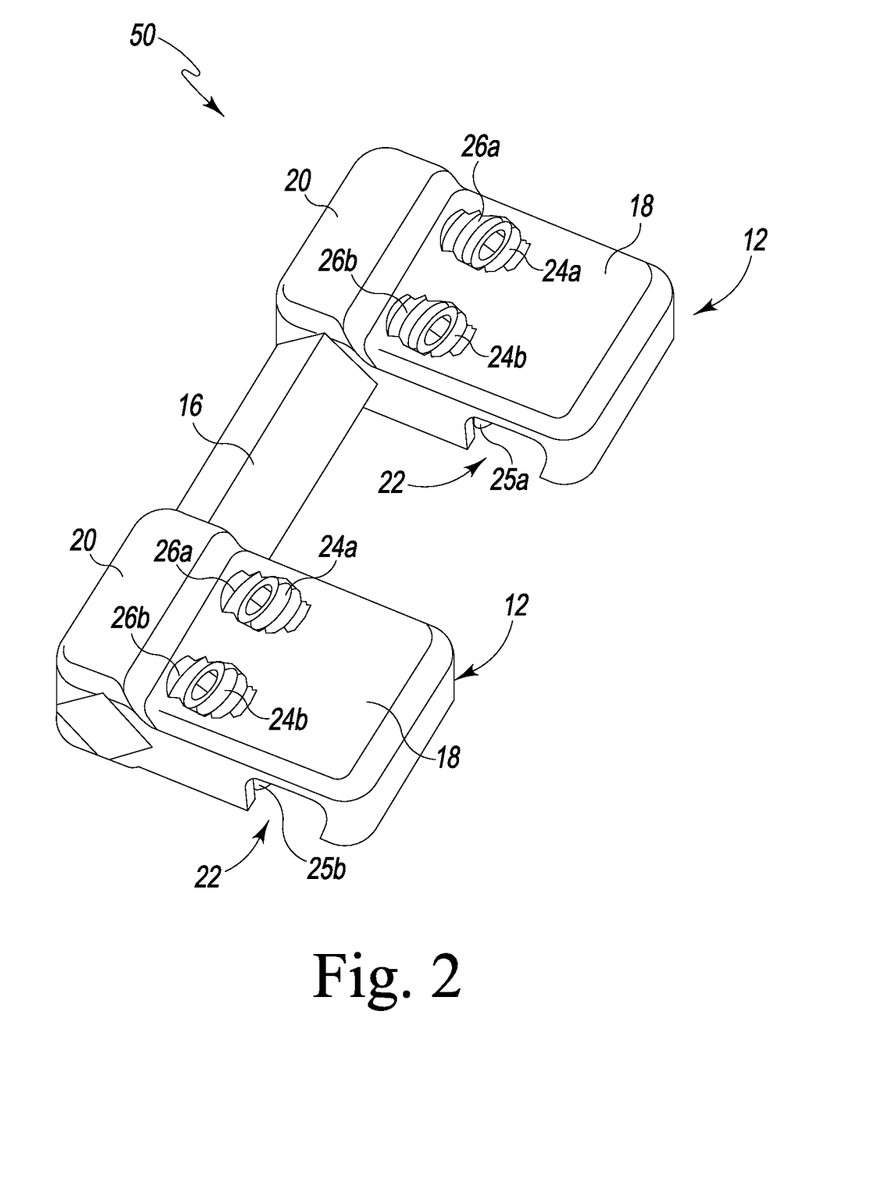
FIG. 2 is an isometric view of another exemplary embodiment of a supplementary spinal fixation/stabilization device providing dynamic intervertebral connection fashioned in accordance with the present principles.

Referring to FIG. 2 there is depicted another exemplary embodiment of a spine or spinal implant embodied as a supplemental or supplementary spinal fixation/stabilization apparatus or device that provides dynamic intervertebral connection (dynamic supplemental or supplementary spinal fixation/stabilization apparatus) generally designated 50 fashioned in accordance with the principles of the present invention. The dynamic supplemental spinal fixation/stabilization apparatus 50 is formed of a suitable biocompatible material.

The dynamic supplemental spinal fixation/stabilization apparatus 50 is characterized by an attachment device or connector 12 that is configured, adapted and/or operative to connect, attach or couple to a previous fusion (e.g. a spine rod, not shown, of a spinal rod fixation device, not shown), a resilient and/or elastomeric connector 16 that is configured, adapted and/or operative to flex and/or bend, and a secondary attachment device or connector 12 that is configured, adapted and/or operative to connect, attach or couple to an adjacent vertebral level in order to prevent it from degenerating further.

The attachment device 12 is made from a biocompatible material such as titanium, stainless steel, PEEK (polyetheretherketone) or the like. The attachment device 12 is formed as a generally rectangular body 18 (other shapes being contemplated) with a generally annular channel or groove 22 extending from one end of the body 18 to the other end of the body 18. The channel 22 is configured to be received on or onto a spinal rod. The attachment device 12 also includes a first set screw 24a that is situated in a first bore 26a. The first bore 26a extends from a top or upper side or surface of the body 18 to a lower or under side or surface of the body 18 that intersects in, terminates in, or opens into the channel 22. The first bore 26a angles into the channel 22 from the upper side of the body 18. The first set screw 24a extends through the first bore 26a and provides contact with the spinal rod that is seated in the channel 22 (see FIG. 2 where end 25b of second set screw 24b can be seen extending into the channel 22). The first set screw 24a thus fixes (or aids in fixing) the attachment device 12 to the spinal rod.

The attachment device further includes a second set screw 24b that is situated in a second bore 26b. The second bore 26b extends from the top or upper side or surface of the body 18 to the lower or under side or surface of the body 18 that intersects in, terminates in, or opens into the channel 22. The second bore 26b angles into the channel 22 from the upper side of the body 18. The second set screw 24b extends through the second bore 26b and provides contact with the spinal rod that is seated in the channel 22 (again, see FIG. 2 where end 25b of second set screw 24b can be seen extending into the channel 22). The second set screw 24b thus fixes (or aids in fixing) the attachment device 12 to the spinal rod.

The attachment device 12 moreover includes a reinforced or raised rear portion 20 through which one end of the elastomeric connector 16 extends and/or is received (an end of which can be seen in FIG. 2). The elastomeric connector 16 is non-rotatably held by the portion 20 and is shown as a generally square (rectangular) rod whose shape aids in preventing twisting or rotation between the attachment device 12 and the secondary attachment device 12. The other end of the connector 16 is received by/in the secondary attachment device 12. Particularly, the other end of the connector 16 is non-rotatably received by or in reinforced or raised rear portion 20 through which one end of the elastomeric connector 16 extends and/or is received.

The attachment device 12 is fixed to an existing spinal fixation/stabilization assembly while the secondary attachment device 12 is fixed to an adjacent level spinal fixation device. The elastomeric connector 16 thus provides flexing or bending relative to the attachments devices 12, 12 and thus between the vertebrae to which they are fixed.

Figure 3:
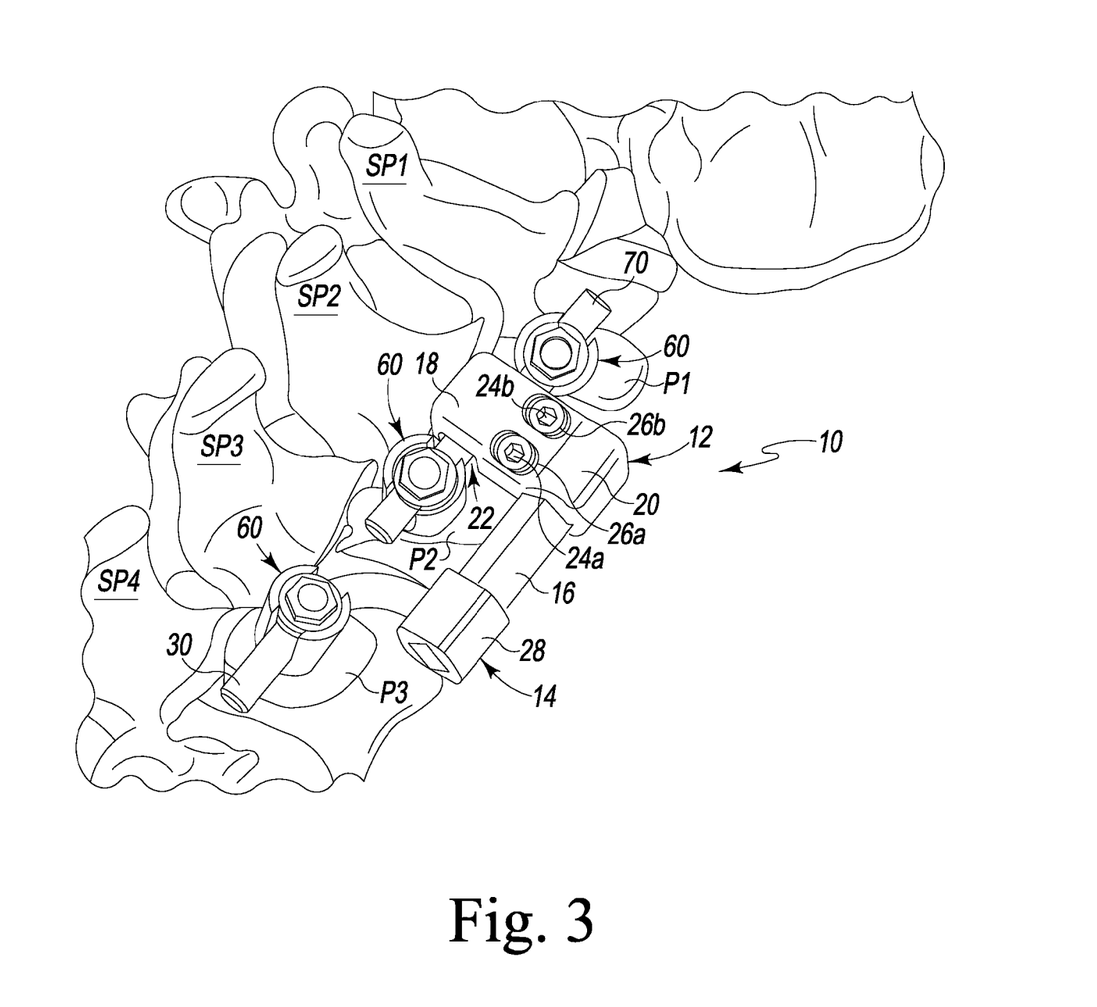
FIG. 3 is an isometric view of a portion of a human spine having the supplementary spinal fixation/stabilization device of FIG. 1 connected to an existing spinal fixation construct and a spinal bone screw assembly each of which are affixed to lateral portions of adjacent vertebrae of the spine.

FIG. 3 depicts the dynamic supplemental spinal fixation/stabilization apparatus 10 affixed to spinal fixation/stabilization constructs on one lateral side of the spine to provide additional, supplemental or supplementary fixation/stabilization between one fixation portion of the spine (i.e. vertebrae V1 and V2 labeled through their spinous processes SP1 and SP2) and another portion of the spine; namely adjacent vertebra (vertebra V3 labeled through its spinous process SP3). Particularly, FIG. 3 depicts an existing spinal fixation/stabilization construct, fixing/stabilizing two adjacent vertebrae, defined by a spine rod 70 held by and between two adjacent vertebral bone screw assemblies 60 (located on pedicles P1 and P2 of adjacent vertebrae), and an additional vertebral level; namely vertebral bone screw assembly 60 (located on a lower adjacent vertebra pedicle P3), hence inter-vertebral. The dynamic supplemental spinal fixation/stabilization apparatus 10 is shown on one lateral side of the vertebrae with the attachment device 12 affixed to the spinal rod 70 wherein the set screws 24a, 24b engage the spinal rod 70. The rod 30 of the secondary attachment device 14 is held by a vertebral bone screw assembly 60 affixed on the pedicle P3 of a lower adjacent vertebra. The supplementary spinal implant 10 thus provides dynamic fixation between the first level of fixation/stabilization (two adjacent vertebrae) and an additional lower vertebral level.

Figure 4:
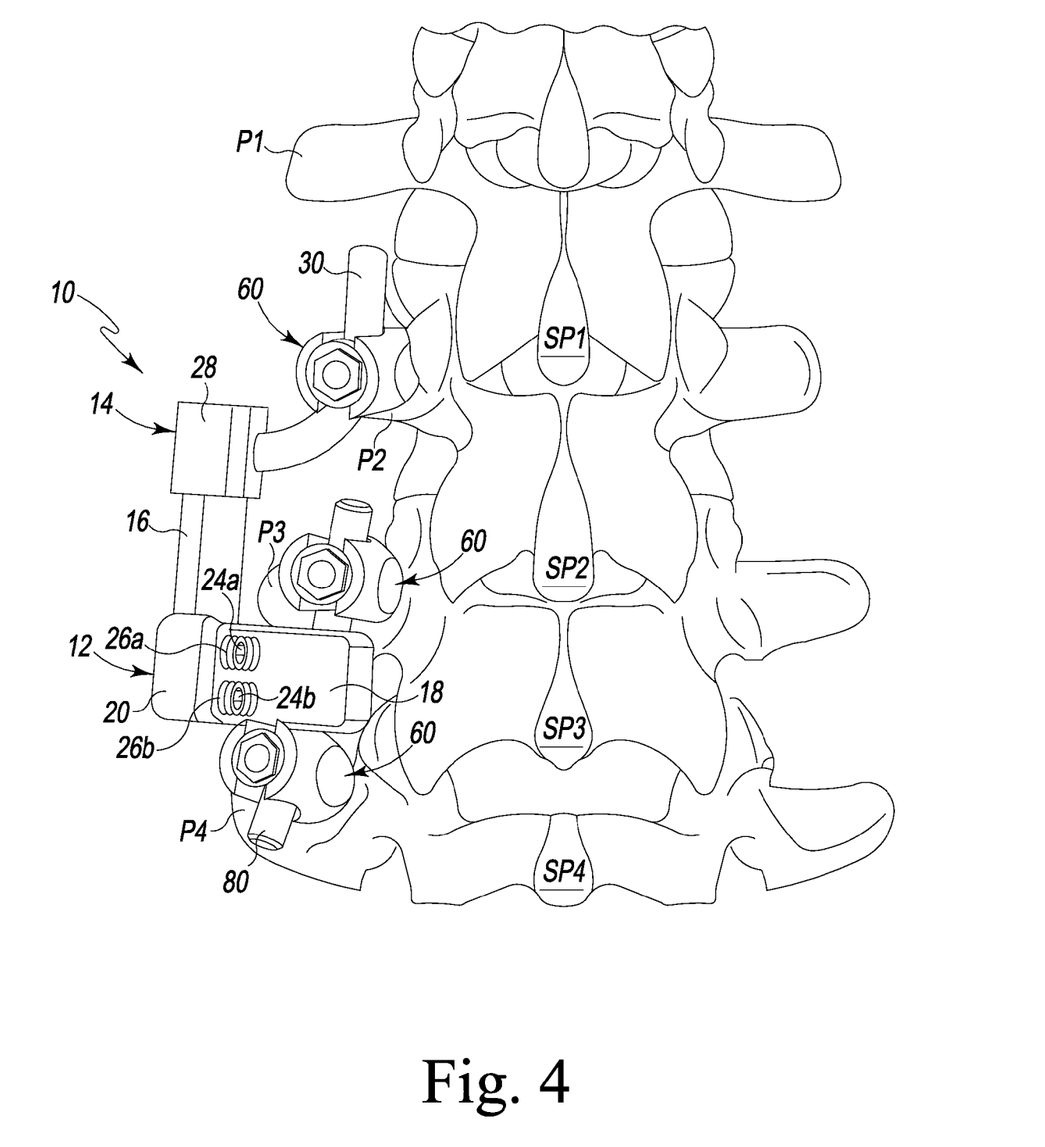
FIG. 4 is an isometric view of a portion of the human spine having the supplementary spinal fixation/stabilization device of FIG. 1 connected to another existing spinal fixation construct and a spinal bone screw assembly each of which are affixed to lateral portions of adjacent vertebrae.

FIG. 4 depicts the dynamic supplemental spinal fixation/stabilization apparatus 10 affixed to spinal fixation/stabilization constructs on another lateral side of the spine to provide additional, supplemental or supplementary fixation/stabilization between one fixation portion of the spine (i.e. vertebrae V4 and V3 labeled through their spinous processes SP4 and SP3) and another portion of the spine; namely adjacent vertebra (vertebra V2 labeled through its spinous process SP2). Particularly, FIG. 4 depicts an existing spinal fixation/stabilization construct, fixing/stabilizing two adjacent vertebrae, defined by a spine rod 80 held by and between two adjacent vertebral bone screw assemblies 60 (located on pedicles P4 and P3 of adjacent vertebrae), and an additional vertebral level; namely vertebral bone screw assembly 60 (located on an upper adjacent vertebra pedicle P2), hence inter-vertebral. The dynamic supplemental spinal fixation/stabilization apparatus 10 is shown on one lateral side of the vertebrae with the attachment device 12 affixed to the spinal rod 80 wherein the set screws 24a, 24b engage the spinal rod 80. The rod 30 of the secondary attachment device 14 is held by a vertebral bone screw assembly 60 affixed on the pedicle P2 of an upper adjacent vertebra. The supplementary spinal implant 10 thus provides dynamic fixation between the first level of fixation/stabilization (two adjacent vertebrae) and an additional upper vertebral level.

Figure 5:
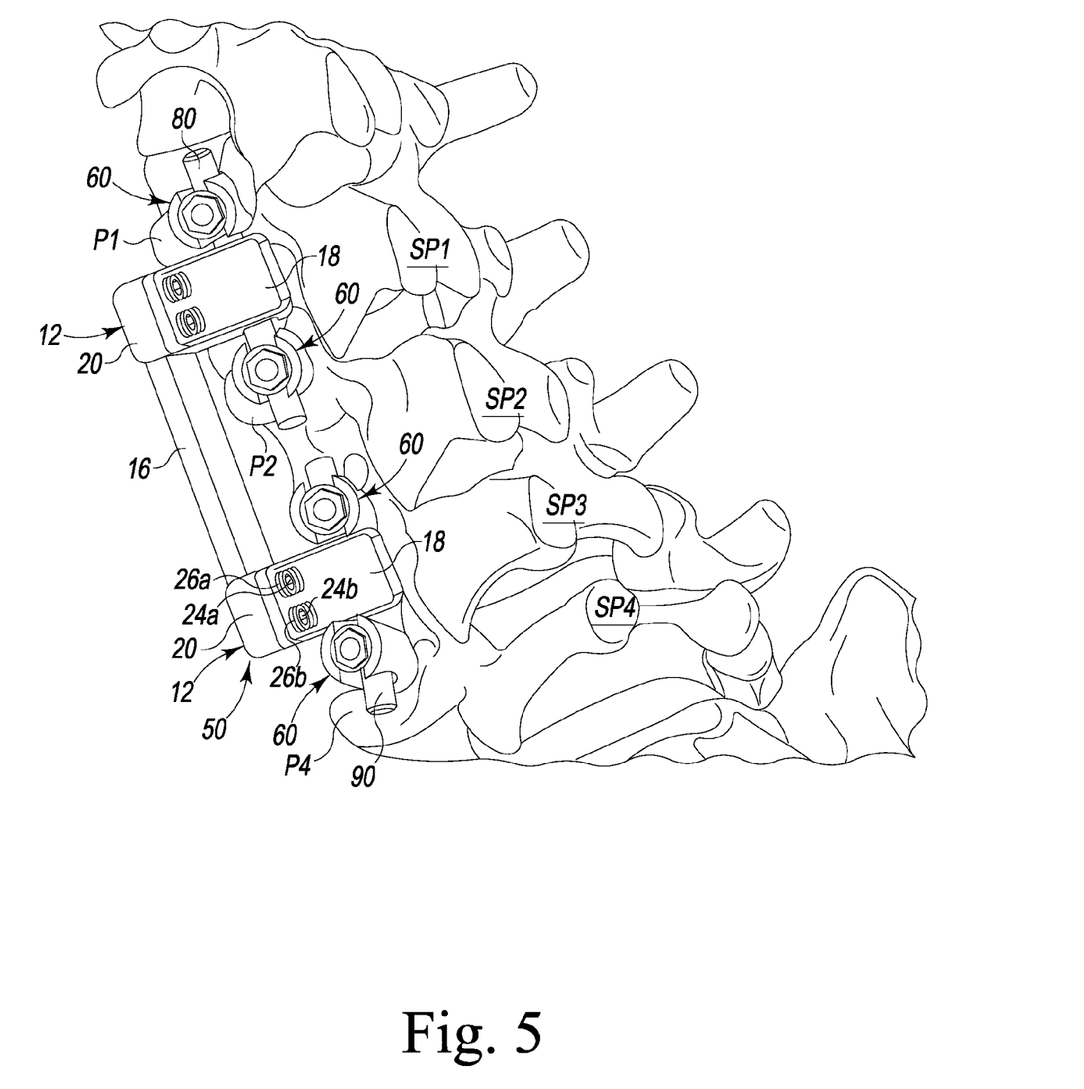
FIG. 5 is an isometric view of a portion of the human spine having the supplementary spinal fixation/stabilization device of FIG. 2 connected to two existing spinal fixation constructs each of which are affixed to lateral portions of adjacent vertebrae.

FIG. 5 depicts the dynamic supplemental spinal fixation/stabilization apparatus 50 affixed to two separate spinal fixation/stabilization constructs on one lateral side of the spine to provide additional, supplemental or supplementary fixation/stabilization between one fixation portion of the spine (i.e. vertebrae V1 and V2 labeled through their spinous processes SP1 and SP2) and another fixation portion of the spine (vertebra V3 and V4 labeled through their spinous process SP3 and SP4). Particularly, FIG. 5 depicts two existing spinal fixation/stabilization constructs, each fixing/stabilizing two adjacent vertebrae, with one construct defined by a spine rod 80 held by and between two adjacent vertebral bone screw assemblies 60 (located on pedicles P1 and P2 of adjacent vertebrae), and another construct defined by a spine rod 90 held by and between two adjacent vertebral bone screw assemblies 60 (located on pedicles P3 and P4 of adjacent vertebrae); hence inter-vertebral. The dynamic supplemental spinal fixation/stabilization apparatus 50 is shown on one lateral side of the vertebrae with the attachment device 12 affixed to the spinal rod 80 wherein the set screws 24a, 24b engage the spinal rod 80 and the other attachment device 12 affixed to the spinal rod 90 wherein the set screws 24a, 24b engage the spinal rod 90. The supplementary spinal implant 50 thus provides dynamic fixation between the first level of fixation/stabilization (two adjacent vertebrae) and an additional level of fixation/stabilization (two adjacent vertebrae) that are adjacent the first level of fixation/stabilization.

Figure 6:
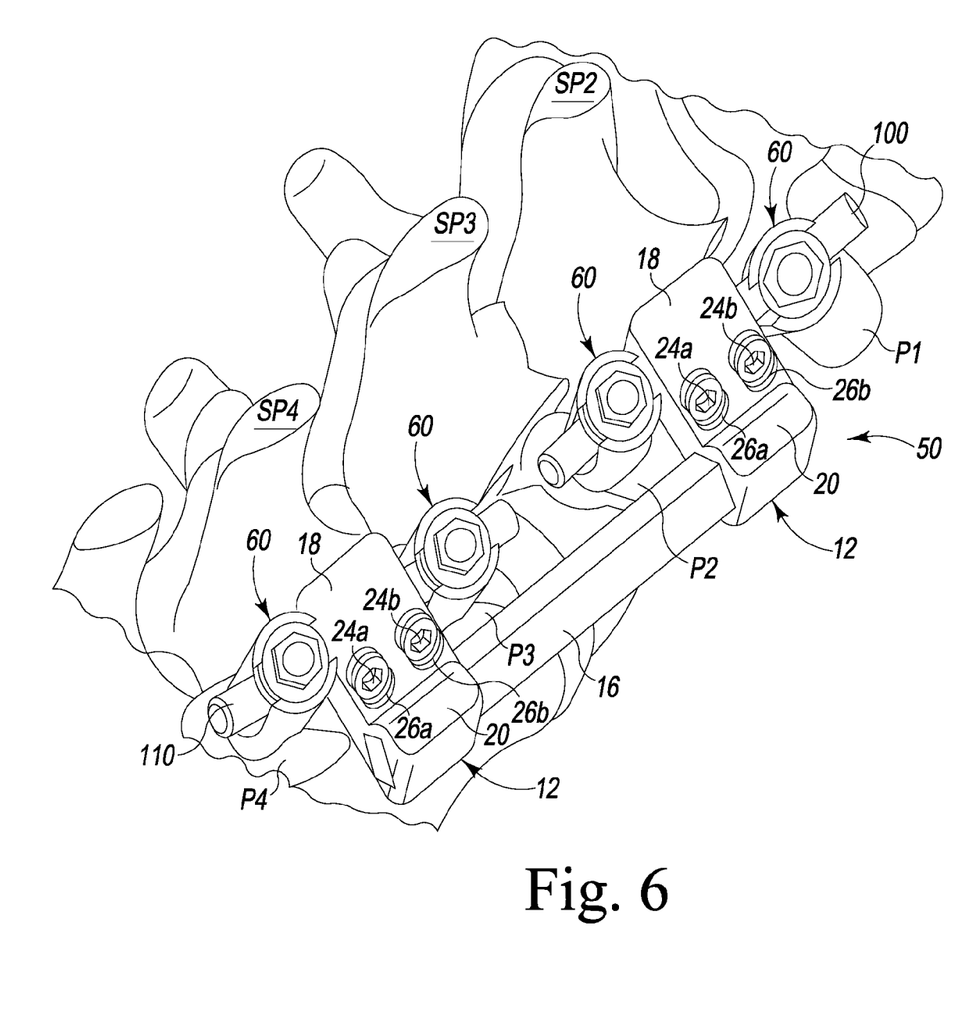
FIG. 6 is isometric view of a portion of the human spine having the supplementary spinal fixation/stabilization device of FIG. 2 connected to two other existing spinal fixation constructs each of which are affixed to lateral portions of adjacent vertebrae.

FIG. 6 depicts the dynamic supplemental spinal fixation/stabilization apparatus 50 affixed to two separate spinal fixation/stabilization constructs on another lateral side of the spine to provide additional, supplemental or supplementary fixation/stabilization between one fixation portion of the spine (i.e. vertebrae V1 and V2 labeled through their spinous processes SP1 and SP2) and another fixation portion of the spine (vertebra V3 and V4 labeled through their spinous process SP3 and SP4). Particularly, FIG. 6 depicts two existing spinal fixation/stabilization constructs, each fixing/stabilizing two adjacent vertebrae, with one construct defined by a spine rod 100 held by and between two adjacent vertebral bone screw assemblies 60 (located on pedicles P1 and P2 of adjacent vertebrae), and another construct defined by a spine rod 110 held by and between two adjacent vertebral bone screw assemblies 60 (located on pedicles P3 and P4 of adjacent vertebrae); hence inter-vertebral. The dynamic supplemental spinal fixation/stabilization apparatus 50 is shown on one lateral side of the vertebrae with the attachment device 12 affixed to the spinal rod 80 wherein the set screws 24a, 24b engage the spinal rod 100 and the other attachment device 12 affixed to the spinal rod 110 wherein the set screws 24a, 24b engage the spinal rod 110. The supplementary spinal implant 50 thus provides dynamic fixation between the first level of fixation/stabilization (two adjacent vertebrae) and an additional level of fixation/stabilization (two adjacent vertebrae) that are adjacent the first level of fixation/stabilization.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected and their equivalents.

What is claimed is:

1. A spinal implant comprising:
a first connector configured for attachment to a first spinal implant construct affixed to a lateral side of a spine;
a second connector configured for attachment to a second spinal implant construct affixed to the lateral side of the spine, the second connector comprising a body and a unitary configured rod extending from the body in a direction away from the first connector and toward a distal end of the configured rod, wherein the configured rod includes a bend forming a curved cylindrical exterior surface defining a substantially right angle; and
a resilient connection member coupled to and between the first and second connectors, the resilient connection member being flexible to allow movement of the first and second connectors relative to one another, wherein the resilient connection member includes a rectangular cross-section;
wherein the first connector comprises a top surface forming a unitary structure with a bottom surface generally opposite the top surface, wherein one of the top and bottom surfaces defines a channel configured to receive a first spinal rod of the first spinal implant, and wherein raised portions of the top and bottom surfaces define an area of increased thickness for receiving the resilient connection member between the top and bottom surfaces, the raised portions of the top and bottom surfaces being spaced apart from the channel along the top and bottom surfaces;
wherein the channel is configured such that the distal end of the unitary configured rod and the first spinal rod are substantially parallel when the first spinal rod is received in the channel.

2. The spinal implant of claim 1, wherein the resilient connection member is formed of an elastomeric.

3. The spinal implant of claim 2, wherein the elastomeric comprises PEEK.

4. The spinal implant of claim 1, wherein the second connector is configured for attachment to a bone screw assembly of the second spinal implant.

5. The spinal implant of claim 4, wherein the first connector further includes a set screw for securing the first connector to the first spinal rod.

6. The spinal implant of claim 5, wherein the first connector includes an additional set screw for securing the first connector to the first spinal rod.

7. A dynamic spinal implant comprising:
a first connector configured for attachment to a first existing spinal implant construct affixed to a lateral side of a spine;
a second connector configured for attachment to a second existing spinal implant construct affixed to the same lateral side of the spine;
a unitary configured rod extending from the second connector in a first direction away from the first connector and toward a distal end of the configured rod, wherein the configured rod includes a bend forming a curved exterior surface defining a right angle; and
a resilient connection member coupled to and extending between the first and second connectors, the resilient connection member having a rectangular cross-section and being flexible to allow limited movement of the first and second connectors relative to one another;
wherein the first connector comprises a top surface forming a unitary structure with a bottom surface generally opposite the top surface, wherein one of the top and bottom surfaces defines a channel configured to receive a spinal rod, and wherein raised portions of the top and bottom surfaces define an area of increased thickness for receiving the resilient connection member between the top and bottom surfaces, the raised portions of the top and bottom surfaces being spaced apart from the channel along the top and bottom surfaces;
wherein the channel is configured such that the distal end of the unitary configured rod and the spinal rod are substantially parallel when the first spinal rod is received in the channel.

8. The dynamic spinal implant of claim 7, wherein the resilient connection member is formed of an elastomeric.

9. The dynamic spinal implant of claim 8, wherein the elastomeric comprises PEEK.

10. The dynamic spinal implant of claim 7, wherein the second connector is configured for attachment to a bone screw assembly of the second existing spinal implant construct.

11. The dynamic spinal implant of claim 10, wherein:
the first connector includes a set screw for securing the first connector to the spinal rod.

12. The dynamic spinal implant of claim 7, wherein the second connector is configured for attachment to a second spinal rod of the second existing spinal implant construct.

13. The dynamic spinal implant of claim 12, wherein:
the first connector includes a first set screw for securing the first connector to the spinal rod.

14. The spinal implant of claim 13, wherein the first connector includes an additional set screw for securing the first connector to the spinal rod.

15. A spinal implant for providing supplementary fixation or stabilization between adjacent fixed or stabilized levels of the spine, the spinal implant comprising:
a first connection device configured for attachment to a first existing spinal implant construct affixed to a lateral side of first and second adjacent vertebrae of a spine;
a second connection device configured for attachment to a second existing spinal implant construct affixed to the same lateral side of a third vertebra of the spine adjacent one of the first and second vertebrae; and
a resilient connection member formed of an elastomeric and coupled to and extending between the first and second connection devices in a linear manner, the resilient connection member having a rectangular cross-section and being flexible to allow limited movement of the first and second connection devices relative to one another;
wherein the first connection device comprises a top surface forming a unitary structure with a bottom surface generally opposite the top surface, wherein one of the top and bottom surface defines a channel configured to receive a spinal rod, and wherein raised portions of the top and bottom surfaces define an area of increased thickness for receiving the resilient connection member between the top and bottom surfaces, the raised portions of the top and bottom surfaces being spaced apart from the channel along the top and bottom surfaces;

wherein the second connection device includes a unitary configured rod including a bend, the bend forming a curved cylindrical exterior surface defining a substantially right angle.

16. The spinal implant of claim 15, wherein the second connection device is configured for attachment to a bone screw assembly of the second existing spinal implant construct.

17. The spinal implant of claim 16, wherein:
the channel includes an elongated rod-shaped cavity configured for reception of the spinal rod and further includes a set screw for securing the first connector to the spinal rod.

18. The spinal implant of claim 15, wherein:
the first connection device is configured for attachment to a first spinal rod of the first existing spinal implant construct and the channel is configured for reception of the first spinal rod of the first existing spinal implant construct, and the first connection device further includes a first set screw for securing the first connection device to the first spinal rod; and
the second connection device is configured for attachment to a second spinal rod of the second existing spinal implant construct and includes an elongated rod-shaped cavity configured for reception of the second spinal rod of the second existing spinal implant construct, and further includes a second set screw for securing the second connection device to the second spinal rod.

* * * * *